(12) United States Patent
Kemp

(10) Patent No.: US 9,492,005 B2
(45) Date of Patent: Nov. 15, 2016

(54) IMPLEMENT HAVING A REACTION AND DELIVERY SYSTEM

(71) Applicant: COLGATE-PALMOLIVE COMPANY, New York, NY (US)

(72) Inventor: James H. Kemp, Basking Ridge, NJ (US)

(73) Assignee: COLGATE-PALMOLIVE COMPANY, New York, NY (US)

( * ) Notice: Subject to any disclaimer, the term of this patent is extended or adjusted under 35 U.S.C. 154(b) by 197 days.

(21) Appl. No.: 14/158,327

(22) Filed: Jan. 17, 2014

(65) Prior Publication Data

US 2014/0133896 A1     May 15, 2014

Related U.S. Application Data

(62) Division of application No. 12/991,592, filed as application No. PCT/US2008/062777 on May 6, 2008, now Pat. No. 8,632,268.

(51) Int. Cl.

| A46B 11/00 | (2006.01) |
| A46B 9/04 | (2006.01) |
| A46B 13/04 | (2006.01) |
| A61K 8/22 | (2006.01) |

(Continued)

(52) U.S. Cl.
CPC ............ *A46B 11/0068* (2013.01); *A46B 9/04* (2013.01); *A46B 11/0003* (2013.01); *A46B 11/0006* (2013.01); *A46B 11/0075* (2013.01); *A46B 13/04* (2013.01); *A61C 17/349* (2013.01); *A61K 8/22* (2013.01); *A61K 8/347* (2013.01); *A61Q 11/00* (2013.01); *A46B 2200/1066* (2013.01); *A61C 17/3436* (2013.01); *A61C 17/3454* (2013.01)

(58) Field of Classification Search
CPC .............. A46B 11/0003; A46B 11/00; A46B 11/0072; A46B 2200/1066; A46B 7/04; A46B 9/04; A46B 13/008
USPC .......................................... 401/47, 132, 270
See application file for complete search history.

(56) References Cited

U.S. PATENT DOCUMENTS 2,155,245 A * 4/1939 Sekine ..................... A46B 9/04
                                                        15/167.1
3,691,585 A * 9/1972 Flom ........................ A46B 1/00
                                                        15/104.94

(Continued)

FOREIGN PATENT DOCUMENTS

| EP | 0 747 114 | 12/1996 |
| WO | WO 03/020159 | 3/2003 |

(Continued)

*Primary Examiner* — Jennifer C Chiang
*Assistant Examiner* — Bradley Oliver

(57) ABSTRACT

A reaction and delivery implement that includes a handle configured for user manipulation, a head having a plurality of agent housing regions, the first agent housing region housing a first agent and the second agent housing region housing a second agent, the first and second agents being different. The head is configured to facilitate both prevention of intermixing of the first and second agents in a storage position as well as reaction of the first and second agents through intermixing in a delivery position so as to produce and apply a third agent to a contacted surface when in the delivery position. The reaction and delivery implement may be an oral care implement such as a toothbrush. The implement may also be motorized and may be used with a wide array of reactions.

17 Claims, 6 Drawing Sheets

(51) Int. Cl.
  *A61K 8/34* (2006.01)
  *A61Q 11/00* (2006.01)
  *A61C 17/34* (2006.01)

(56) References Cited

U.S. PATENT DOCUMENTS

| | | | |
|---|---|---|---|
| 4,320,221 | A | 3/1982 | Hoffman |
| 4,849,213 | A | 7/1989 | Schaeffer |
| 5,373,599 | A | 12/1994 | Lemon et al. |
| 5,605,676 | A | 2/1997 | Gaffar et al. |
| 5,836,769 | A | 11/1998 | Spencer |
| 6,105,587 | A | 8/2000 | Dunn |
| 6,116,900 | A | 9/2000 | Ostler |
| 6,735,803 | B2 * | 5/2004 | Kuo ............... A46B 7/04 15/22.1 |
| 7,182,542 | B2 | 2/2007 | Hohlbein |
| 7,575,387 | B2 | 8/2009 | Atkin |
| 7,877,833 | B2 | 2/2011 | Gavney, Jr. |
| 8,109,686 | B2 | 2/2012 | Bartschi et al. |
| 2001/0002228 | A1 | 5/2001 | Owens |
| 2001/0046477 | A1 | 11/2001 | Wolfe |
| 2003/0044604 | A1 | 3/2003 | Weihrauch |
| 2003/0066145 | A1 | 4/2003 | Prineppi |
| 2006/0159509 | A1 | 7/2006 | Grez et al. |
| 2006/0236477 | A1 | 10/2006 | Gavney, Jr. |
| 2007/0134045 | A1 | 6/2007 | Holt et al. |
| 2008/0008728 | A1 | 1/2008 | Atkin |
| 2008/0014010 | A1 | 1/2008 | Bartschi et al. |
| 2009/0060622 | A1 | 3/2009 | Lian et al. |

FOREIGN PATENT DOCUMENTS

| | | |
|---|---|---|
| WO | WO 2007/025012 | 3/2007 |
| WO | WO 2007/073917 | 7/2007 |
| WO | WO 2007/076405 | 7/2007 |
| WO | WO 2007/109136 | 9/2007 |

* cited by examiner

IMPLEMENT HAVING A REACTION AND DELIVERY SYSTEM

CROSS-REFERENCE TO RELATED APPLICATIONS

The present application is a divisional of U.S. patent application Ser. No. 12/991,592, filed on Nov. 8, 2010, which in turn is a national stage entry under 35 U.S.C. §371 of International Patent Application No. PCT/US2008/062777, filed May 6, 2008, the entireties of which are hereby incorporated by reference.

BACKGROUND

The present invention pertains to a reaction and delivery implement. In particular the implement may be a brush configured to facilitate reaction of a plurality of initial substances and further configured to deliver the substance resulting from the reaction to a desired receiving surface.

Various delivery implements including various brushes are known. Brushes are commonly used for application of a substance to any of a number of surfaces. For example, brushes such as toothbrushes are used in oral care to clean food particles from teeth and to apply toothpaste and other oral care substances to the surface of the teeth. Brushes are also used in home care applications such as painting or staining of various surfaces. Brushes may also be used for application of cosmetics especially in application of certain makeup and other substances to the skin of users, and the face in particular.

BRIEF SUMMARY

Exemplary embodiments according to the present disclosure are directed to an implement having a chemical delivery system for delivering an agent.

In one aspect, the invention can be a toothbrush, comprising: a handle configured for user manipulation; and a head having a first capsule for retaining a first agent and a second capsule for retaining a second agent, the first and second agents being different, wherein the head includes a plurality of cleaning elements having an alignment and placement between and surrounding each of the first and second capsules that prevents intermixing of the first and second agents in a storage mode, and that facilitates intermixing of the first and second agents so as to produce and apply a third agent to a surface during use of the toothbrush.

In another aspect, the invention can be a brush, comprising: a handle configured for user manipulation; and a head having a plurality of housing regions, including a first housing region having a first agent and a second housing region for retaining a second agent, the first housing region being a region of cleaning elements having the first agent on the cleaning elements and the second housing region being a sealed structure surrounded by the region of cleaning elements, the first and second agents being different, wherein the head is configured to prevent intermixing of the first and second agents in a storage mode, and during use of the brush, the head enables intermixing of the first and second agents so as to produce and apply a third agent to a surface.

In yet another aspect, the invention can be a motorized brush, comprising: a handle configured for user manipulation; and a head having a plurality of agent housing regions including a first moveable tuft plate for retaining a first agent on a first cleaning element and a second moveable tuft plate for retaining a second agent on a second cleaning element, the first and second movable tuft plates moving in opposing direction, the first and second agents being different, wherein the head is configured to facilitate both prevention of intermixing of the first and second agents in a storage position as well as reaction of the first and second agents through intermixing in a delivery position by movement of the first and second moveable tuft plates so as to produce and apply a third agent to a contacted surface when in the delivery position.

In a further aspect, the invention can be a toothbrush comprising: a handle configured for user manipulation; a head having a first store of oral care material and a second store of oral care material, wherein the head includes a plurality of cleaning elements having an alignment and placement between and surrounding each of the first and second stores of oral care material that prevents intermixing of the first and second stores of oral care material in a storage mode; and wherein the first and second stores of oral care material comprise a gel in a fluidic state prior to use of the toothbrush.

BRIEF DESCRIPTION OF THE DRAWINGS

The features, and advantages of the invention will be apparent from the following more detailed description of certain embodiments of the invention and as illustrated in the accompanying drawings in which.

DETAILED DESCRIPTION

In the following description, the invention is discussed in terms of an implement with a reaction and delivery system and more particularly in the form of a brush, toothbrush or various oral care implements. However, the implement with a reaction and delivery system is also contemplated to take the form of any of various specific embodiments with the principles described herein.

The inventive aspects may illustratively be shown or described in the form of a toothbrush (e.g. a form of an oral care implement) but could also be in the form of other personal care implements. For example, a toothbrush can be used for personal hygiene, such as oral care purposes. Alternatively, the reaction and delivery implement may be utilized. It is understood that other embodiments may be utilized and structural and functional modifications may be made without departing from the scope of the present invention.

Figure 1:
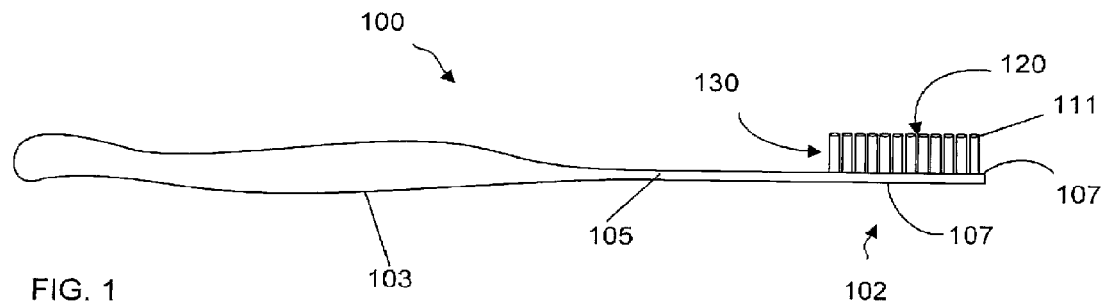
FIG. 1 is a schematic illustration of a toothbrush according to an embodiment of the invention.
Figure 2:
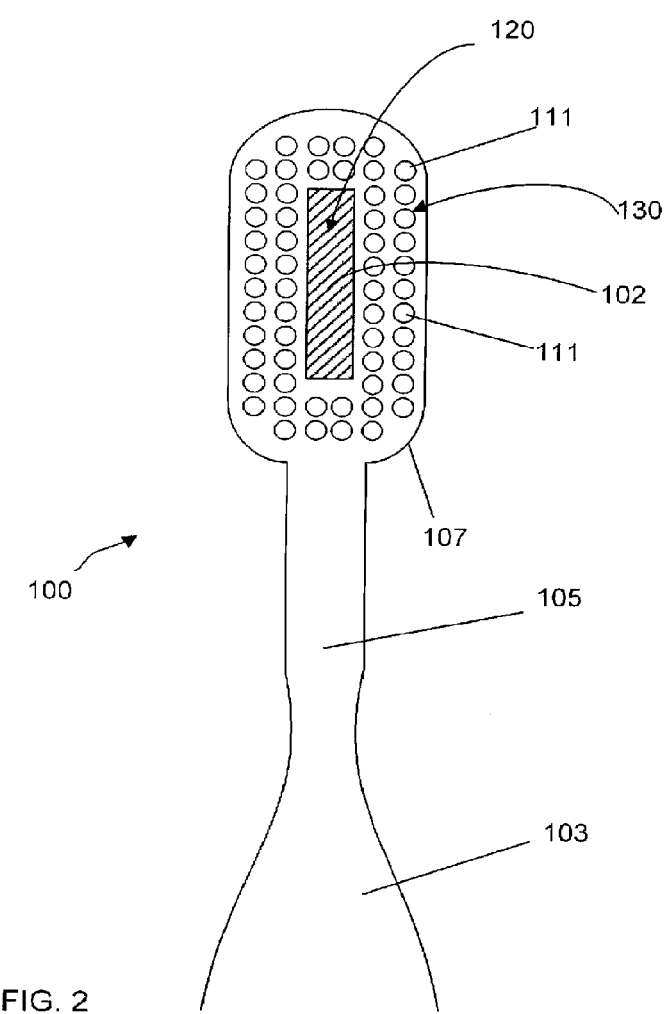
FIG. 2 is a front elevational view of the head of the toothbrush shown in FIG. 1.

FIGS. 1-2 illustrate an oral care implement, such as a toothbrush, generally designated with the reference numeral 100. The toothbrush 100 generally includes a head 102 and a handle 103. The handle 103 is generally an elongated member dimensioned so that a user can readily grip and manipulate the toothbrush 100. The handle 103 may be formed of many different shapes, lengths and with a variety of constructions. In one construction, the handle 103 has a neck portion 105 positioned adjacent the head 101. The neck portion 105 may be a narrowed region on the handle 103 between head 101 and the part of the handle normally gripped by the user. Nevertheless, the neck portion 105 could be the region between the head 101 and the part of the handle normally gripped by the user. In another construction, the handle 103 is integrally formed with the head 101. Other attachment configurations also are possible.

In FIGS. 1-2, the head 102, includes and houses first and second agent housing regions 120 and 130. First and second housing regions 120 and 130 generally are portions of an implement configured to house a plurality of agents distinct from one another in a first position or state and then facilitate intermixing and reaction of a first and second agent, for example, to form a third agent. Because certain effective agents, medicaments, anesthetics, antimicrobial agents, polishes, paints, whiteners, and other miscellaneous agents, substances and chemicals lose effectiveness over time, it is desirable to apply them fairly immediately after their formation. However, in many instances it is difficult or even impossible to transport the supply of core components and agents needed to form the desirable effective agent. Accordingly, an implement is desirable that can house core components in a cost-effective manner and facilitate application of an effective agent formed by reacting or mixing of two or more initial agents.

For example, in FIG. 2, a first agent is housed in the first agent housing region 120 within a sealed structure in the generally central region of the toothbrush. Various sealed structures may include structures manufactured coincident with the manufacture of toothbrush 100. The sealed structure may have various mechanisms for releasing the first agent. The sealed structure may include a wearable exterior surface or portion of an exterior surface so that it erodes due to mechanical abrasion during use of the toothbrush 100. Also, the seal structure may be formed of a water-soluble material to chemically erode in an oral cavity during use of the toothbrush. Accordingly, in one construction, an outer layer may include a water-soluble polymer (such as polyethylene oxide, polyethylene glycol, or polyvinyl alcohol). Other known, non-toxic polymers with a controllable water solubility that is sufficient at bio-effective levels can be used as is known in the art.

Depending on the desired use of the implement, the solubility of the polymer used in the outer layer may be modified. For example, if the implement is desired to be a repeated use implement, materials with solubility low enough so that they dissolve out slowly over a period of many uses may be chosen. Alternatively, if the entire quantity of agent is desired for a particular reaction and/or if the implement is a single use implement, the solubility of materials is preferably high. While the solubility characteristics have been described in reference to the oral cavity and water, these principles are clearly contemplated in other contexts where the material housing the first agent can be degraded either by physical engagement or solubility in an environmental liquid, chemical or other environmental characteristic. For example, the sealed structure may be degraded when exposed to high temperature, or a certain chemical or a structure with sharper edges such as a tooth.

The medium containing the agent can be incorporated into a sealed reservoir during manufacture of the toothbrush, in which case the toothbrush can be disposed of after the supply of the agent is exhausted. Alternatively, the reservoir 11 can be refillable through an inlet (not shown), and/or can be replaceable, e.g., by inserting a replaceable cartridge into a recess in the toothbrush. The cartridge can be spring-loaded to stay in place after insertion, and can have a seal to prevent unwanted leakage of the agent.

While the first agent housing region in the toothbrush of FIGS. 1-2 is a sealed structure, the second agent housing region 130 is a region of cleaning elements. As shown, the head 101 may include an oral care region comprising one or more tooth cleaning elements 111. As used herein, the term "tooth cleaning elements" or "cleaning elements" includes any type of structure that is commonly used or is suitable for use in providing oral health benefits (e.g., tooth cleaning, tooth polishing, tooth whitening, massaging, stimulating, etc.) by making contact with portions of the teeth and gums. Such tooth cleaning elements include but are not limited to tufts of bristles that can be formed to have a number of different shapes and sizes and elastomeric cleaning members that can be formed to have a number of different shapes and sizes, or a combination of both tufts of bristles and elastomeric cleaning members. While certain bristle configurations are illustratively depicted, it should be understood that any bristle configuration and any handle configuration can be used.

In one construction, the one or more tooth cleaning elements 111 are formed from a plurality of bristles. Referring to FIGS. 1 and 2, the tooth cleaning elements 111 form bristle regions that may have the same shape or may also have different shapes. However, it is understood that a number of different configurations of oral care implements may be utilized. The one or more tooth cleaning elements 111 may be attached to the head 101 by known methods, such as being fit within recesses formed in the head 101 along a front portion 107 of the toothbrush 100 (FIGS. 1 & 2).

Here, the cleaning elements 111 shown in the schematic of FIGS. 1-2 are of a material that facilitates housing an agent. These cleaning elements may be of a material with a tactile or sticky texture to hold the second agent or alternatively the cleaning elements may be formed with grooves, ledges, holes, hollows, or other features and/or surface structure, shape or configuration that facilitate housing of a powder, liquid, gel, or other forms of agent for eventual reaction with the first agent when the implement, here a toothbrush, is put into use.

Figure 3:
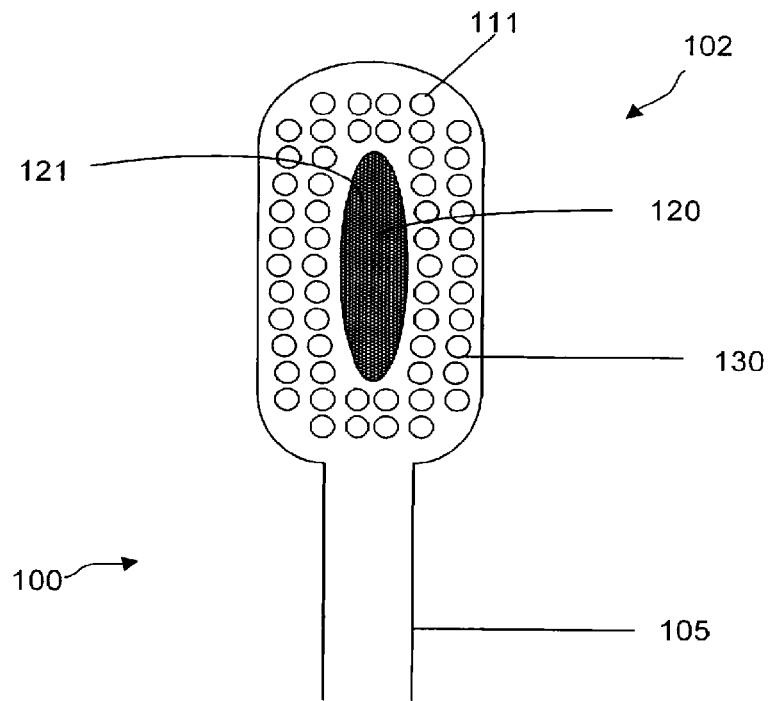
FIG. 3-10 are further front elevational views of further embodiments of the head of the toothbrush shown in FIG. 1.
Figure 4:
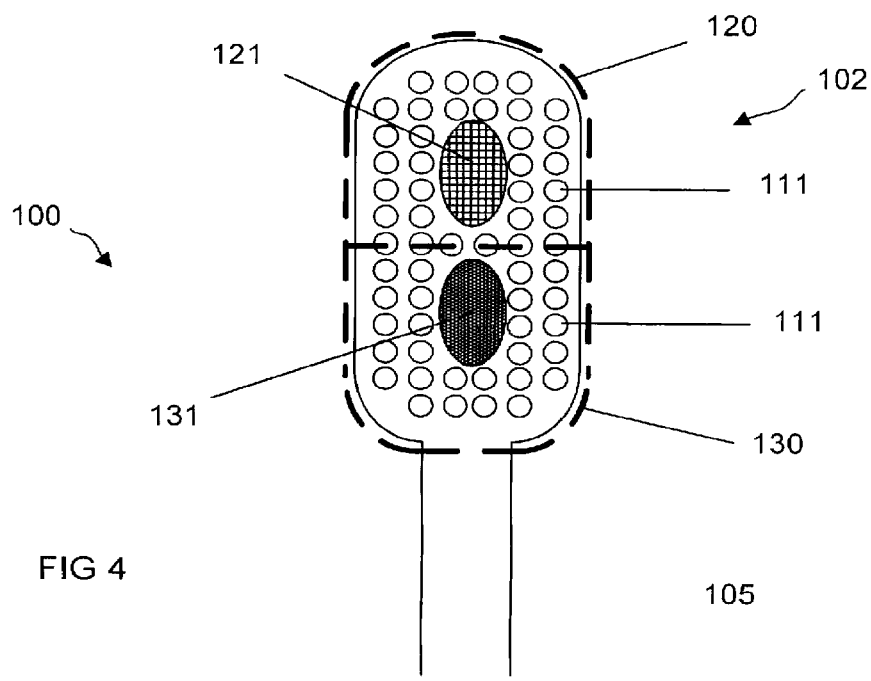

FIGS. 3 and 4 are further illustrative examples of a reaction and delivery implement. Here, a capsule is utilized as one or more of the agent housing regions. In FIG. 3 the toothbrush 100 is configured such that a removable capsule can be housed in the central region of the front portion 107 of the head 102. In accordance with the principles described herein, a first agent housing region 120 here is provided in the form of a capsule 120. The capsule may take many specific forms shapes, size, colors and textures. For example, the capsule may have color of specific draw or attention to children. Likewise, the capsule may be color coded to coincide with flavors such as red for strawberry or green for lime. Additionally, the capsule may be composed of an outer structure for housing medicaments and numerous other reactive agents as is described herein. Capsules have good traits of mobility and typically will not rupture until ingested or purposefully punctured. Accordingly, the capsule may house various agents until the capsule is punctured to release its contents or until a liquid such as saliva or water causes the outer shell or membrane to dissolve or disintegrate. As shown in FIG. 3, a second agent housing region 130 is a region of cleaning elements 111 that may be configured to hold a second agent. When a user contacts the head 102, and in particular the bristles or cleaning elements 111, to a user's teeth in the oral cavity, the capsule 120 may be punctured. Additionally, further puncture assisting structure may be built into the head of the toothbrush specifically underneath the capsule housing region so as to facilitate and expedite puncture of the capsule upon contact or engagement.

Either soon after puncture or dissolving of a portion of the capsule, the first agent initially housed within the capsule 120 and the second agent housed on the cleaning elements 111 in the second agent housing region 130 are mixed and reacted to form a third agent. Typical movements of the toothbrush 100 such as a typical brushing motion or gum massaging motion further intermix the two agents thereby facilitating reaction and delivery of the third agent or resultant as desired.

FIG. 4 also depicts a toothbrush 100 housing a capsule. In this construction, two capsules are housed on the head 102. As shown in FIG. 4, broken lines have been used to identify the first and second agent housing regions 120 and 130 respectively. Accordingly, each of the first and second housing regions 120 and 130 in FIG. 4 includes a capsule and a plurality of cleaning elements surrounding the capsule. As illustrated by the contrast in fill of the schematic capsules, each of the capsules in the first and second agent housing regions 120 and 130 contains a distinct agent. Intermixing and delivery of the agents regarding the illustrative embodiment of FIG. 4 may be accomplished in a similar manner and/or related manners as described with regard to FIG. 3. Further, here the placement and alignment of the bristles 111 between the capsules and surrounding the capsules facilitate intermixing and delivery as the bristles will bend and sway back and forth in normal use when contacted with a solid surface or structure and accordingly the agent from one capsule will be transferred to an area at or near the second capsule. Likewise, agent from the second capsule will be transferred to an area at or near the first capsule. Through the repeated motions of brushing or cleaning or gumming or other related oral care activities, the first and second agents are thereby intermixed to create a third agent and the third agent is delivered by direct contact via the bristles or cleaning elements 111 or related structure to a location of desired delivery. As is appreciated by those of skill in the art, various bristle configurations, capsule arrangements and positioning and related configurations are contemplated and may be utilized.

Figure 5:
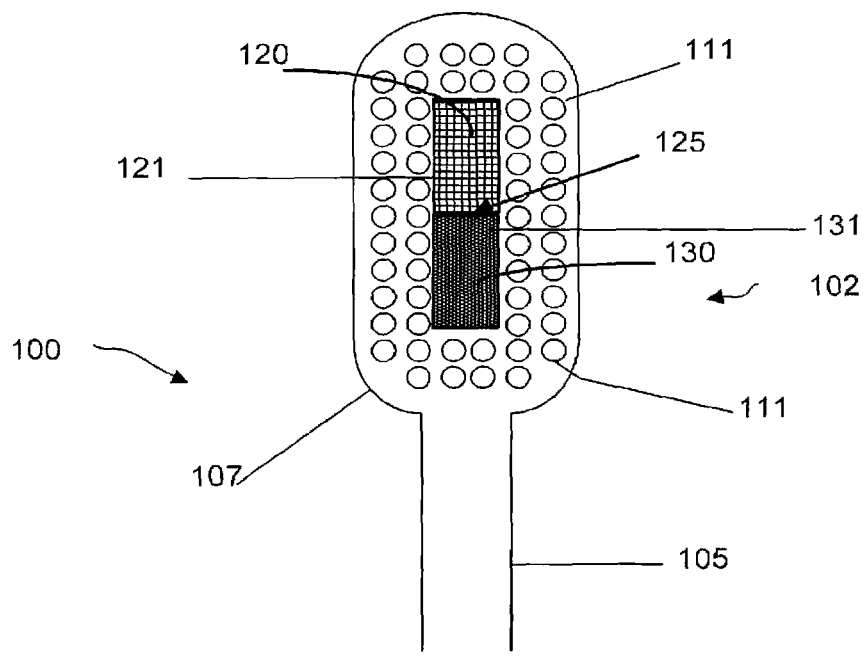

In a further construction, FIG. 5 illustrates a toothbrush 100 in which the first and second agent housing regions are containment structures separated by a barrier 125 to prevent intermixing of the agents that are housed on opposing sides of the barrier. Each containment structure may be of any of a number of specific structures. For example, the first agent housing region 120 may include a containment structure 121 composed of a sponge like substance for housing a first agent while the second agent housing region 130 may include a containment structure 131 formed of a variety of densely packed small bristles. Capsules, pills and other structures may be considered containment structures. Here, the first and second agent housing regions are positioned as abutted and adjacent structures. They may either be integrally formed as part of the head 102 and/or toothbrush 100 or removable by various known mechanisms such as snap-on, slide or screw in attachment.

Because of the close proximity of the first and second agents in the non-mixed or storage position, it may be desirable to separate these agents with a barrier. This barrier 125 may take any of a number of appearances or configurations. Among the illustrative embodiments contemplated is a soluble membrane or a slide away membrane akin to a sliding door. Accordingly, in a storage position or mode, the first and second agent housing regions 120 and 130 and their associated containment structures 121 and 131 are held in distinct sections by the barrier. In operational use, the barrier 125 is either removed by a user prior to use of the toothbrush 100 or else incidentally removed during use either through dissolving of destruction of the membrane or else by incidental removal during use of the toothbrush. The barrier 125, in place, allows two reactive agents to be housed in tight, small or close configurations without risking contamination well in advance of the desired intermixing to form a third agent and the associated delivery. Further, the barrier and proximal housing of the two agents facilitates a more efficient use of the first and second agents and is advantageous if one or more of the agents is expensive or may cause detrimental effects if a person ingests too large a quantity. Closer proximate housed agents facilitate more successful or efficient intermixing especially when reactions require fairly exact quantities of constituents or when an agent has limited quantities such as whitening components in cosmetic applications or medicaments in first aid treatment. As understood by one of skill in the art, containment structures such as those referenced and described with respect to FIG. 5 may be any of a number of structures beyond those specifically described. For example, capsules, wafer, gelatinous formations, or candy-type structures that dissolve over time, and recesses or depressions all may be considered variations of containment structures in any given embodiment or configuration.

Figure 6:
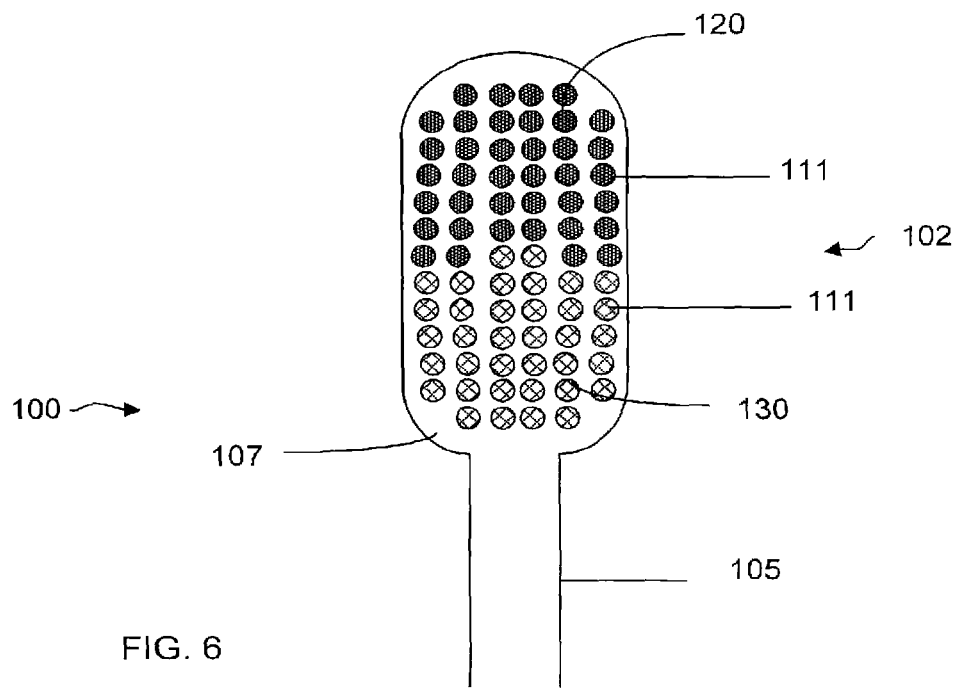
Figure 7:
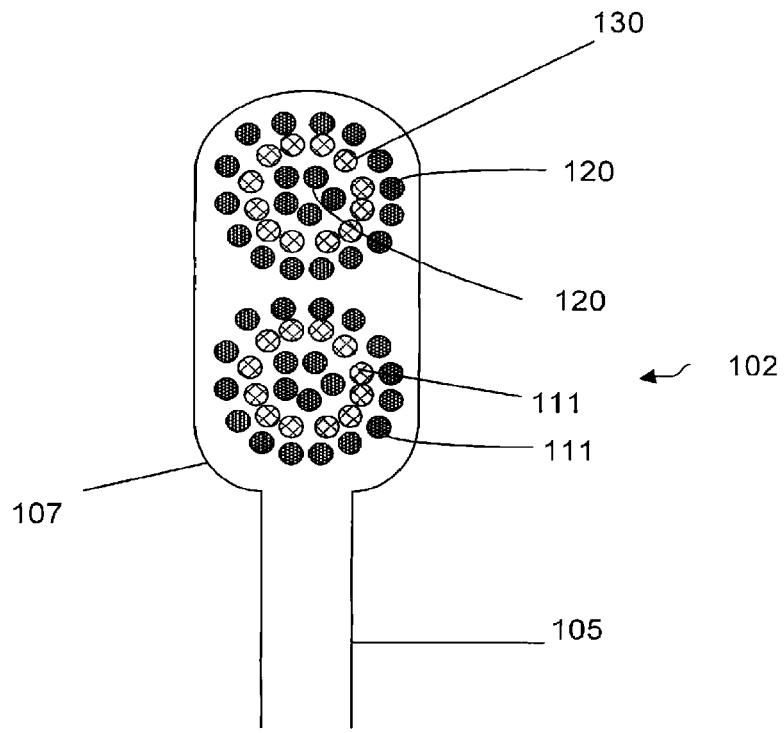
Figure 8:
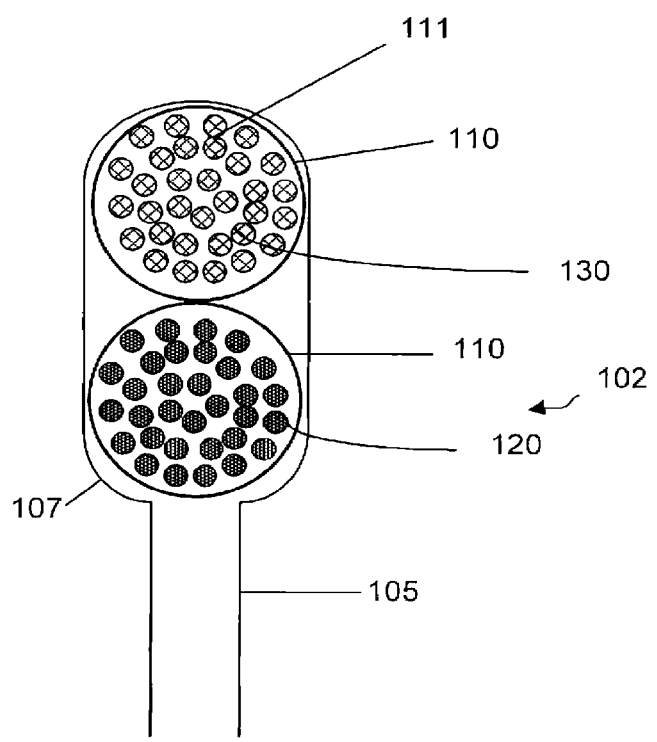

FIGS. 6-8 illustrate a reaction and delivery implement in which the substantial entirety of both the first and second agent housing regions 120, 130 are made up of cleaning elements 111 such as bristles. To further facilitate clarity and understanding, the first agent housing region 120 is exclusively shown and formed by a cluster or grouping of illustratively darker shaded bristles while the second agent housing region is shown and formed by a illustratively lighter shaded cluster or grouping of lighter shaded bristles. It is understood that all of the bristles containing like shading contain a like agent (e.g., the first agent). Accordingly, FIG. 6 illustrates an embodiment in which a first agent is housed on the top half of the head 102 within the first agent housing region 120 while a second distinct agent is housed on the lower half of the head 102 within the second agent housing region 130. In certain applications, ready intermixing is not desired as one or more agents may be volatile and thus prone to reaction prematurely if a more definitive separation is not present. Additionally, in order to allow for low cost implements to be produced a more generic pattern of bristles such as shown in FIG. 6 may be preferred to an embodiment in which the agents are more intermingled and thus manufacturing may be more complex and costly.

FIG. 7 illustrates a configuration in which generally concentric rings of bristles, each individually or collectively forming agent housing regions, are provided. By housing agents in concentric rings as shown, intermixing for certain applications may be improved due to the further significant dispersion of the agent. Accordingly, the agents may intermix more thoroughly and more quickly as compared to a configuration in which 2 distinct regions share a single boundary such as that shown in FIG. 6.

FIG. 8 illustrates a further embodiment of toothbrush 100 for reaction and delivery of two agents. While somewhat similar in bristle configuration to FIG. 7, here bristles housing a first agent and second agent are provided in two distinct clusters in a storage state and until the toothbrush 100 is put in use. Bristles 111 housing a first agent are again illustratively shown in darker shading while bristles housing a second agent are shown in lighter shading. Each of the clusters of bristles in the toothbrush of FIG. 8 is housed on a tuft plate 110. These tuft plates may integrally formed upon formation of the head or alternatively they may distinct components that in certain configurations are removeable and replaceable. Thus, a reusable toothbrush 100 may have a variety of tuft plates and bristle clusters that may be used in varying combinations. Further, the brush may in certain instances be packaged and sold as an oral implement with various refills or user selectable agent housing regions for use and replacement in the oral care implement, here a toothbrush 100. The while clusters of bristles are shown as circular, other shapes are a possible.

Figure 9:
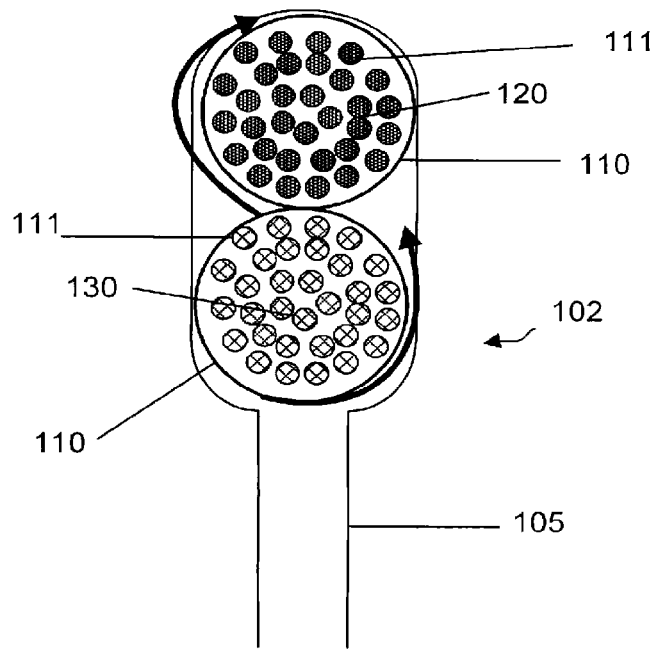
Figure 10:
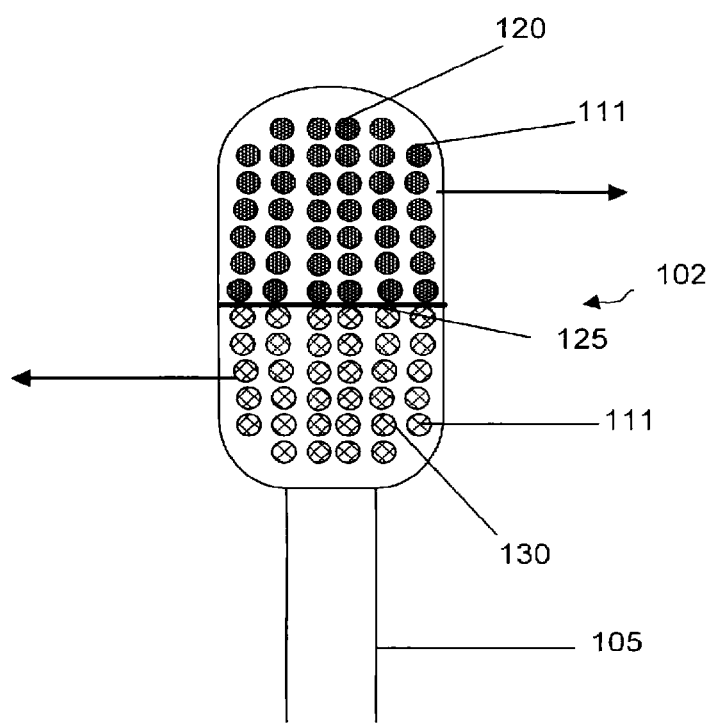

FIGS. 9-10 are heads 102 of a motorized toothbrush 100. In schematic fashion, the arrows in both figures illustrate various contemplated manners of motion. For example, the first and second agent housing regions 120, 130 may be rotated, spun or oscillated as is shown in FIG. 9. Also, the first and second agent housing regions 120, 130 may also be moved in a more rectilinear fashion such as back and forth movement in opposing directions or back and forth while vibrating. These and other manners of movement are known to those skilled in the art and may be utilized here accordingly. This motorized movement further enhances the reaction and mixing of the first and second agents as well as delivery of a third agent formed from the reaction. For example, motorized vibration or frictional engagement of bristles with a first agent and a second agent may help expedite or help perfect mixing of the two agents due to the enhanced speed, force and repetition of mixing.

Figure 11:
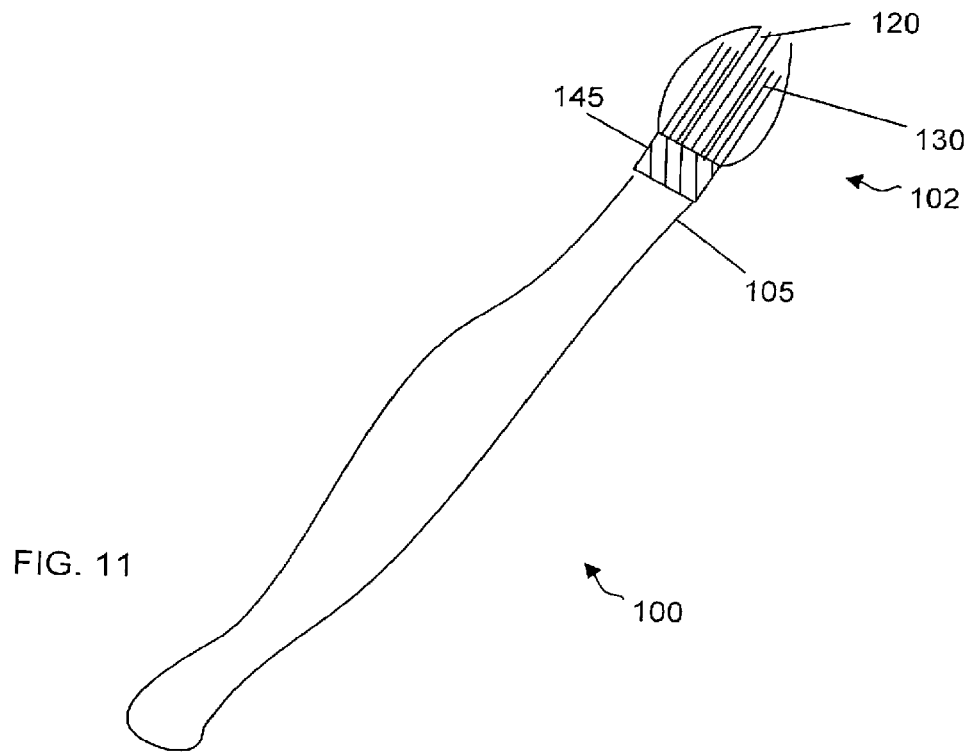
FIGS. 11-12 are perspective and top plan views respectively of a brush including the reaction and delivery system illustratively described in FIGS. 1-12.
Figure 12:
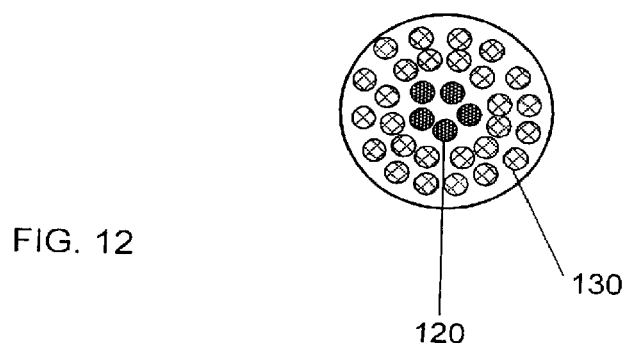

FIGS. 11 and 12 illustrate another oral care implement for reaction of first and second agents and delivery of a third resulting agent formed from the reaction of the first and second agents as described above with respect to FIGS. 1-10. Here, the first agent housing region 120 is positioned in the central region of a brush while the second agent housing region 130 circumscribes the first agent housing region 120. Here bristles 111 housing the agents form the agent housing regions 120, 130. In this particular configuration, the regions may be reacted by squeezing, bending, and/or rubbing the bristles. The bending of the bristles and rubbing will release the agents housed within the respective regions 120, 130 and allow for intermixing. The configuration of this brush is especially conducive for delivery of paints or whitening agents based upon its elongated bristles 111 extending from a collar 145 on the neck connected to the handle 103.

While generally first, second and third agents have been referenced throughout the application, it is understood and contemplated that a number of reactions and first, second and third agents are specifically contemplated. Further reactions of first and second agents and subsequent delivery of the third resulting agent of agents not specifically listed herein is contemplated with the principles described herein. For illustrative purposes only below is a list of first, second and third agents respectively such that a first agent when reacted or combined with the second agent via any of the implements or like implements to those of FIGS. 1-12 will result in a third agent that may be delivered to a desired surface. Further the order of the first agent is merely illustrative as first and second agents may be reversed. Further, first and second agent housing region are terms used that may be swapped or reversed with the principles herein. Further, for clarity and ease of explanation the list of examples below is denoted as first agent "(1)" plus (+) second agent "(2)" equals third agent "(3)".

EXAMPLES

First aid—The delivery of cyanoacrylates to open wounds to hasten closure and to further cleanliness of wound is contemplated. Another illustrative example contemplated is the delivery of antimicrobial agents or medicaments to external wounds to facilitate enhanced bacteriological cleanliness or healing.

Surgery—The delivery of antimicrobial agents or medicaments inside wounds or surgical openings to facilitate enhanced bacteriological cleanliness or healing is contemplated.

Lubrication—The delivery of lubricants mechanical functions such as automobiles, weaponry, etc., in civil, governmental or military applications is contemplated.

Adhesives—The delivery of adhesives to organic and inorganic surfaces is contemplated.

Cosmetics—The delivery of make-up, nail polish or cosmetic products or attributes is contemplated.

Paints—The delivery of paints and primers to small areas or surfaces is contemplated.

Numerous other areas of use are contemplated with the principles, examples and embodiments described and disclosed herein. Further, one of ordinary skill in the art would recognize application of these principles in various other contexts and environments not specifically described herein.

Below is a listing of some illustrative reactions contemplated for accomplishment with the described implements: a) (1) a base+(2) an acid=(3) a neutral; b) (1) a base+(2) a curing agent=3) epoxy resin; c) (1) Bisphenol F+(2) Epichchlorhydin=(3) diglycidyl ether of bisphenol A (epoxy resin); d) (1) Calcium carbonate+(2) Hydrogen Peroxide= (3) Peroxide; e) (1) Water+(2) Hydrogen Peroxide=(3) Peroxide; f) (1) Potassium Nitrate+(2) Stannous Fluoride=(3) Sensitivity agents; g) (1) Chlorhexadine+(2) Silica=(3) Antimicrobial agents; h) (1) Cetylpyridinium Chloride+(2) Silica=(3) Antimicrobial agents; i) (1) Triclosan+(2) Pryophosphate=(3) Antimicrobial agents; j) (1) First Flavor+(2) Second Flavor=(3) Third Flavor. For example, as shown above, various agents may be formed that are known for their whitening, cleaning, anti-microbial, taste or other desirable effects. The above list is merely illustrative and various other like or similar reactions are known to those of skill in the art.

It will be understood that while the invention has been described in conjunction with specific embodiments thereof, the foregoing description and examples are intended to illustrate, but not limit the scope of the invention. Other aspects, advantages and modifications will be apparent to those skilled in the art to which the invention pertains, and these aspects and modifications are within the scope of the invention and described and claimed herein.

What is claimed is:

1. A brush, comprising:
a handle configured for user manipulation; and
a head extending along a longitudinal axis and having a plurality of housing regions including a first housing region having a first agent and a second housing region having a second agent, the first housing region being a first grouping of cleaning elements having the first agent integrated thereon and being free of the second agent and the second housing region being a second grouping of cleaning elements having the second agent integrated thereon and being free of the first agent;
wherein a subset of the cleaning elements of the first grouping is directly adjacent to a subset of the cleaning elements of the second grouping;
wherein the first and second agents are different; and
wherein the head is configured to prevent intermixing of the first and second agents in a storage mode, and during use of the brush, the head enables intermixing of the first and second agents so as to produce and apply a third agent to a surface.

2. The brush of claim 1, wherein the first grouping of cleaning elements is located on a distal region of the head and the second grouping of cleaning elements is located on a proximal region of the head, wherein the subset of the cleaning elements of the first grouping are the proximal-most cleaning elements of the first grouping, and wherein the subset of the cleaning elements of the second grouping are the distal-most cleaning elements of the second grouping.

3. The brush of claim 1, wherein the cleaning elements of the first grouping and the cleaning elements of the second grouping are aligned together in longitudinal columns, each longitudinal column having one or more cleaning elements of the first grouping and one or more cleaning elements of the second grouping.

4. The brush of claim 3, wherein for each longitudinal column, one of the cleaning elements of the first grouping is directly adjacent to one of the cleaning elements of the second grouping.

5. The brush of claim 1, wherein the first and second groupings of cleaning elements are arranged in rows extending transversely across the head, and wherein at least one of the rows includes cleaning elements of the first grouping and cleaning elements of the second grouping.

6. The brush of claim 5, wherein in the at least one of the rows that includes cleaning elements of the first grouping and cleaning elements of the second grouping, the cleaning elements of the second grouping are located between the cleaning elements of the first grouping.

7. The brush of claim 5, wherein only one of the rows includes cleaning elements of the first and second groupings, the remaining rows including only cleaning elements of the first grouping or only cleaning elements of the second grouping.

8. The brush of claim 1, wherein the first grouping of cleaning elements are housed on a first tuft plate that is coupled to the head and the second grouping of cleaning elements are housed on a second tuft plate that is coupled to the head.

9. The brush of claim 8, wherein each of the first and second tuft plates is separately removably coupled to the head.

10. The brush of claim 8, wherein the first grouping of cleaning elements are arranged in a plurality of concentric rows on the first tuft plate and wherein the second grouping of cleaning elements are arranged in a plurality of concentric rows on the second tuft plate.

11. A motorized brush, comprising:
a handle configured for user manipulation; and
a head extending along a longitudinal axis and having a plurality of agent housing regions including a first moveable tuft plate comprising a plurality of first cleaning elements having a first agent thereon and a second moveable tuft plate comprising a plurality of second cleaning elements having a second agent thereon, the plurality of first cleaning elements being free of the second agent and the plurality of second cleaning elements being free of the first agent, the first and second movable tuft plates being axially spaced apart and moving in opposing direction, the first and second agents being different, wherein the head is configured to facilitate both prevention of intermixing of the first and second agents in a storage position as well as reaction of the first and second agents through intermixing in a delivery position by movement of the first and second moveable tuft plates so as to produce and apply a third agent to a contacted surface when in the delivery position.

12. The motorized brush of claim 11 wherein the first cleaning elements are arranged in a plurality of concentric rows on the first moveable tuft plate and the second cleaning elements are arranged in a plurality of concentric rows on the second moveable tuft plate.

13. The brush of claim 11 wherein the first moveable tuft plate has a first center-point and the second moveable tuft plate has a second center-point, and wherein the first and second center-points are axially spaced apart.

14. A brush, comprising:
a handle configured for user manipulation; and
a head having a plurality of cleaning elements extending therefrom, the plurality of cleaning elements comprising a first grouping of cleaning elements arranged in a first loop and a second grouping of cleaning elements positioned within the first loop;
wherein the first grouping of cleaning elements comprise a first agent thereon and the second grouping of cleaning elements comprise a second agent thereon, the first and second agents being different, the first grouping of cleaning elements being free of the second agent and the second cleaning elements being free of the first agent; and
wherein the head is configured to prevent intermixing of the first and second agents in a storage mode, and during use of the brush, the head enables intermixing of the first and second agents to produce a third agent.

15. The brush of claim 14 further comprising a third grouping of cleaning elements arranged in a second loop that surrounds the first loop, the third grouping of cleaning elements comprising the second agent thereon.

16. The brush of claim 15 wherein the first and second loops are concentric.

17. The brush of claim 14 wherein the first grouping of cleaning elements comprises tufts of bristles that retain the first agent directly thereon and wherein the second grouping of cleaning elements comprises tufts of bristles that retain the second agent directly thereon.

* * * * *